United States Patent
Garms et al.

(10) Patent No.: US 9,689,812 B2
(45) Date of Patent: Jun. 27, 2017

(54) SYSTEMS AND METHODS FOR GENERATING TWO-DIMENSIONAL IMAGES FROM PROJECTION DATA

(71) Applicant: Morpho Detection, LLC, Newark, CA (US)

(72) Inventors: Walter Irving Garms, Berkeley, CA (US); Sondre Skatter, Oakland, CA (US)

(73) Assignee: MORPHO DETECTION, LLC, Newark, CA (US)

(*) Notice: Subject to any disclaimer, the term of this patent is extended or adjusted under 35 U.S.C. 154(b) by 230 days.

(21) Appl. No.: 14/514,585

(22) Filed: Oct. 15, 2014

(65) Prior Publication Data

US 2016/0109388 A1 Apr. 21, 2016

(51) Int. Cl.
- *A61B 6/00* (2006.01)
- *G01N 23/04* (2006.01)
- *G06T 11/60* (2006.01)
- *G06T 11/00* (2006.01)

(52) U.S. Cl.
CPC .......... *G01N 23/046* (2013.01); *G06T 11/005* (2013.01); *G06T 11/60* (2013.01); *G01N 2223/401* (2013.01); *G06T 2207/10081* (2013.01); *G06T 2207/20216* (2013.01); *G06T 2211/421* (2013.01)

(58) Field of Classification Search
CPC .......... G01N 2223/401; G01N 23/046; G01N 23/04; G01T 11/005; G06T 2207/10081; G06T 2207/20216; G06T 2211/421; G06T 11/005
See application file for complete search history.

(56) References Cited

U.S. PATENT DOCUMENTS

| | | |
|---|---|---|
| 5,881,122 A | 3/1999 | Crawford et al. |
| 6,980,681 B1 | 12/2005 | Hsieh |
| 7,330,528 B2 | 2/2008 | Jefferson |
| 7,492,845 B2 | 2/2009 | Chou et al. |
| 7,515,675 B2 | 4/2009 | Garms et al. |
| 8,437,447 B2 | 5/2013 | Muenker |

(Continued)

FOREIGN PATENT DOCUMENTS

EP 1302164 A1 4/2003

*Primary Examiner* — David J Makiya
*Assistant Examiner* — Dani Fox
(74) *Attorney, Agent, or Firm* — Armstrong Teasdale LLP (57) ABSTRACT

A method for generating a two-dimensional image of an object using a CT scanner is provided. The method includes selecting an imaging surface for the object, the imaging surface including a plurality of pixels, selecting a viewing direction that is non-parallel to the imaging surface, rotating an x-ray source of the CT scanner around the object through a plurality of views, wherein the x-ray source projects x-rays towards a detector array opposite the x-ray source. For each pixel of the plurality of pixels, the method includes acquiring using the detector array, from the plurality of views, data values for x-rays that pass through the pixel and are within a pre-determined angle from parallel to the viewing direction, and combining the data values acquired for the pixel to calculate a final value for the pixel. The method further includes generating the two-dimensional image of the object based on the calculated final values for each pixel.

20 Claims, 10 Drawing Sheets (56) References Cited

U.S. PATENT DOCUMENTS

| | | |
|---|---|---|
| 8,639,007 B2 | 1/2014 | Naidu et al. |
| 2008/0170662 A1 | 7/2008 | Reinhold |
| 2012/0177273 A1* | 7/2012 | Naidu .................. G06T 11/005 382/131 |
| 2012/0189094 A1 | 7/2012 | Neushul et al. |

* cited by examiner

SYSTEMS AND METHODS FOR GENERATING TWO-DIMENSIONAL IMAGES FROM PROJECTION DATA

BACKGROUND

The embodiments described herein relate generally to imaging objects, and more particularly, to generating two-dimensional images of objects from projection data acquired at multiple views.

In some computed tomography (CT) imaging system configurations, an x-ray source projects a fan-shaped beam which is collimated to lie within an X-Y plane of a Cartesian coordinate system and generally referred to as an "imaging plane". The x-ray beam passes through an object being imaged. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray fan beam intersects the object constantly changes. A group of x-ray attenuation measurements (e.g., projection data), from the detector array at one gantry angle may be referred to as a "view". A "scan" of the object comprises a set of views made at different gantry angles, or view angles, during one or more revolutions of the x-ray source and detector about the object or patient being imaged.

Many modern CT systems are helical scanners (also known as spiral scanners), in which the scanned object is continually moved while the projection data is being acquired. The path of the x-ray source describes a helix with respect to the scanned object. Most helical scanners have multiple rows of detectors, and the x-ray fan is collimated into a cone to illuminate the entire array of detectors. The angle between the x-ray source and the first and last detector rows is referred to as the "cone angle".

The entire scanned volume scanned by the helical scanner can be reconstructed using well known tomographic reconstruction algorithms such as direct Fourier or filtered back projection methods. Many of these techniques require a relatively large amount of computation.

Orthographic and SP-like images can be created from the reconstructed volumetric data by projecting digitally through the reconstructed data. This requires significant additional computation, and the resulting images may have relatively poor resolution, making it difficult to distinguish features of the imaged object.

BRIEF SUMMARY

In one aspect, a method for generating a two-dimensional image of an object using a CT scanner is provided. The method includes selecting an imaging surface for the object, the imaging surface including a plurality of pixels, selecting a viewing direction that is non-parallel to the imaging surface, rotating an x-ray source of the CT scanner around the object through a plurality of views, wherein the x-ray source projects x-rays towards a detector array opposite the x-ray source. For each pixel of the plurality of pixels, the method includes acquiring using the detector array, from the plurality of views, data values for x-rays that pass through the pixel and are within a pre-determined angle from parallel to the viewing direction, and combining the data values acquired for the pixel to calculate a final value for the pixel. The method further includes generating the two-dimensional image of the object based on the calculated final values for each pixel.

In another aspect, a processing device for generating a two-dimensional image of an imaging surface of an object is provided, the imaging surface including a plurality of pixels. The processing device is configured to cause a computer to implement a method including acquiring from a detector array communicatively coupled to the processing device, for each pixel of the plurality of pixels, data values for x-rays that pass through the pixel and are within a pre-determined angle from parallel to a viewing direction, wherein the viewing direction is non-parallel to the imaging surface, wherein the x-rays are emitted from an x-ray source that rotates around the object through a plurality of views, and wherein the data values for the pixel are acquired across the plurality of views, combining the data values acquired for each pixel to calculate a final value for each pixel, and generating the two-dimensional image of the imaging surface based on the calculated final values for each pixel.

In yet another aspect, a CT system for imaging an object is provided. The CT system includes a CT scanner including an x-ray source configured to rotate around the object through a plurality of views and project x-rays towards the object, and a detector array positioned opposite the x-ray source, and a storage medium communicatively coupled to the detector array and encoded with machine readable computer program code for generating a two-dimensional image of an imaging surface of the object, the imaging surface including a plurality of pixels. The storage medium including instructions for causing a computer to implement a method including acquiring from the detector array, for each pixel of the plurality of pixels, data values for x-rays that pass through the pixel and are within a pre-determined angle from parallel to a viewing direction, wherein the viewing direction is non-parallel to the imaging surface, and wherein the data values for the pixel are acquired across the plurality of views, combining the data values acquired for each pixel to calculate a final value for each pixel, and generating the two-dimensional image of the imaging surface based on the calculated final values for each pixel.

DETAILED DESCRIPTION

Using the systems and methods described herein, a two-dimensional image of an object is generated. More specifically, an imaging surface for the object is selected, and a viewing direction that is non-parallel to the imaging surface is selected. Data values for x-rays that pass through pixels in the imaging surface and that are within a predetermined angle from parallel to the viewing direction is acquired. For each pixel, the data values are combined to calculate a final value. A two-dimensional image is generated from the final value. Combining data from multiple views facilitates improving a resolution and a signal to noise ratio of the generated image.

As used herein, raw data refers to the actual data value read from a detector. The raw data depends on the x-ray intensity at the detector, the gain of the detector, and any bias (offset) that is added to the detector value. Furthermore and as also used herein, offset data, gain data, sample data, x-ray intensity, normalized data, converted data, x-ray source position, reconstruction circle, and reconstruction volume are as defined as follows:

Offset data: Raw data measurements collected with the x-ray source off.

Gain data: Raw data measurements collected with the x-ray source on, but with no sample objects in the field of view other than permanently installed objects such as the conveyor belt.

Sample data: Raw data measurements collected with the x-ray source on and a sample object in the field of view.

X-ray intensity: The intensity of the x-ray at each detector. X-ray intensity can be computed as K1*(Sample−Offset)/(Gain−Offset), where K1 is a calibration constant.

Normalized data: A measure of the attenuation of an x-ray beam as it travels through an object. Normalized data can be computed as K2*log((Gain−Offset)/(Sample−Offset)), where K2 is a calibration constant and log( ) is the natural logarithm.

Converted data: Any useful representation of the scan data that may be used for a projection image. In the exemplary embodiment, converted data represents normalized data, but other representations (e.g., sample data, x-ray intensity) may be used.

X-ray source position: The gantry may make several complete rotations during acquisition, creating a spiral trajectory of the x-ray source when viewed with respect to the moving scanned object. X-ray source position in this discussion refers to a single point in the spiral trajectory.

Reconstruction Circle: A circle defined by the x-ray fan as the x-ray tube rotates around an object. For accurate CT reconstruction, an object must be entirely within the reconstruction circle.

Reconstruction Volume: A cylinder in the scanned object's coordinates defined by the reconstruction circle and the length of the bag for which there is sufficient data to reconstruct.

Figure 1:
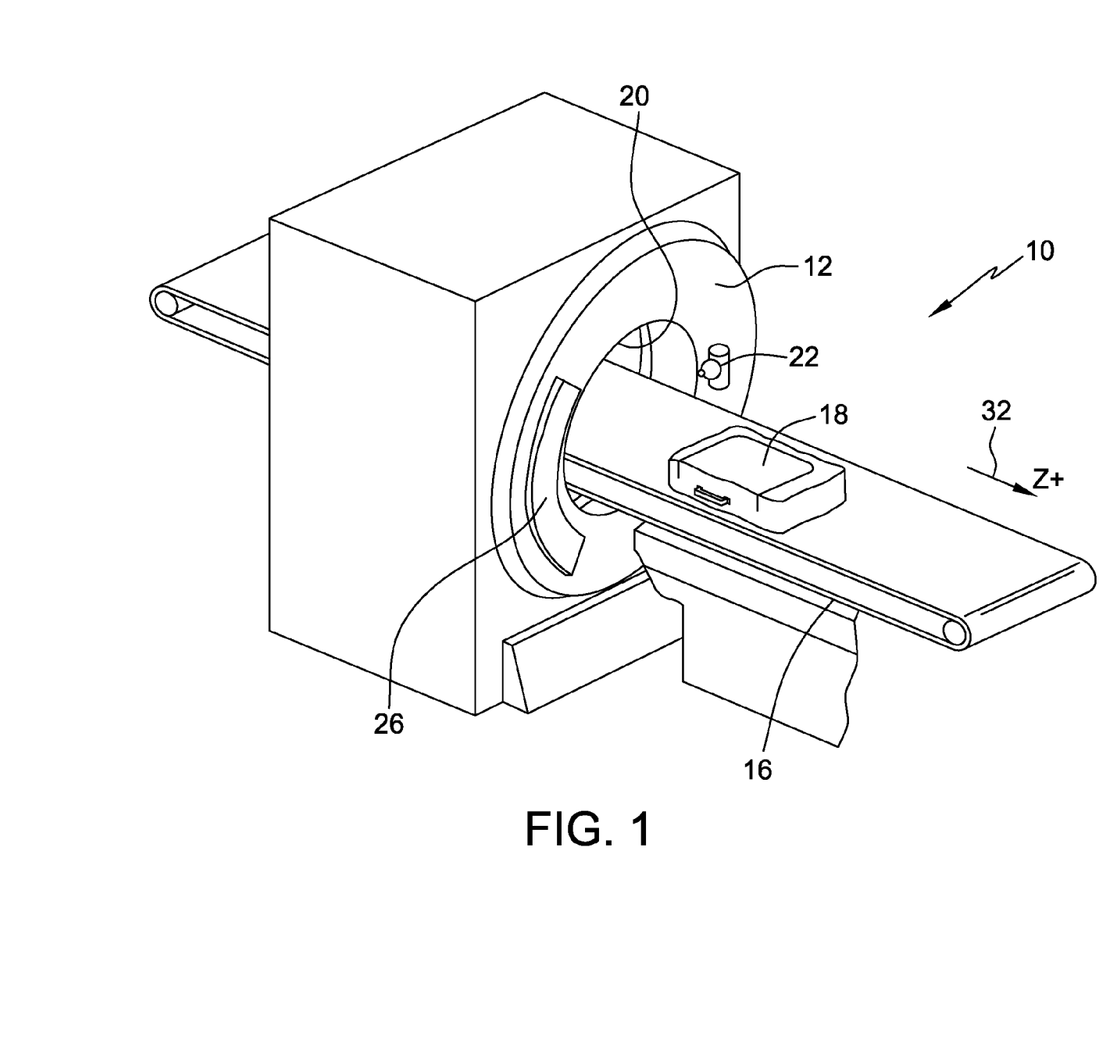
FIG. 1 is a perspective view of an exemplary CT imaging system.
Figure 2:
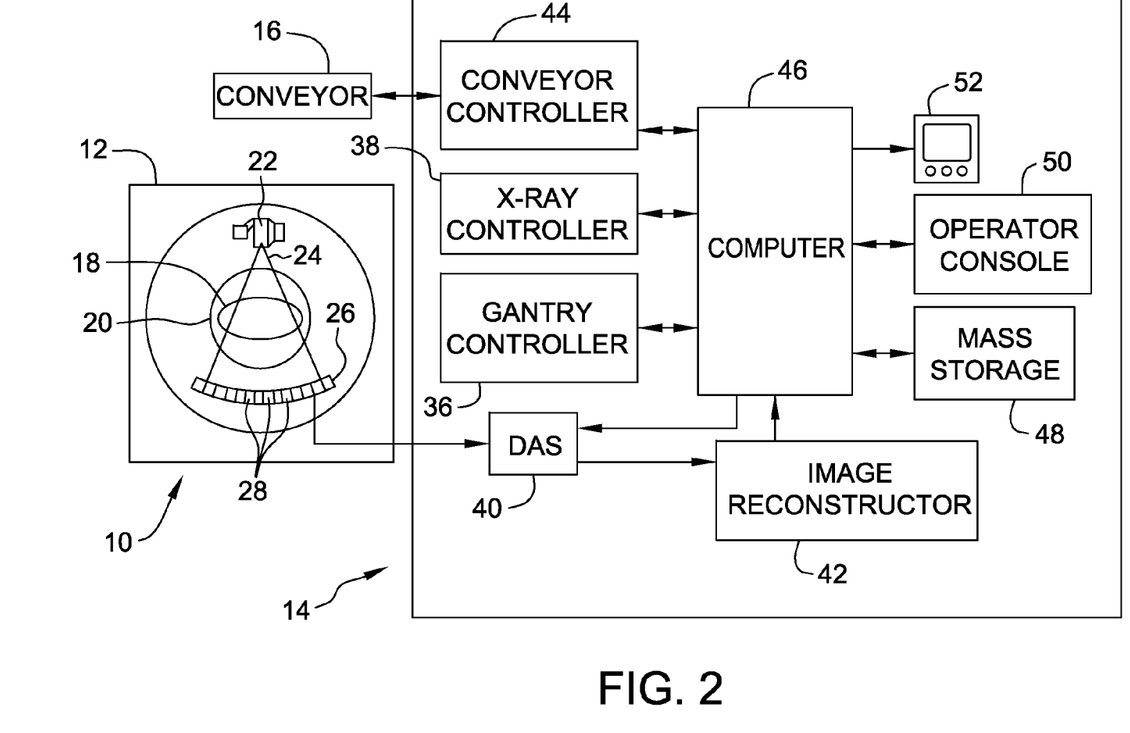
FIG. 2 is a schematic diagram of the CT imaging system shown in FIG. 1.

Referring now to FIGS. 1 and 2, a computed tomography (CT) imaging system 10 is shown. CT imaging system 10 is shown having a gantry 12, which is representative of a CT scanner, a control system 14, and a motorized conveyor belt 16 for positioning an object 18, such as a piece of luggage, in a gantry opening 20 defined through gantry 12. Gantry 12 includes an x-ray source 22 that projects a fan beam of x-rays 24 toward a detector array 26 on the opposite side of gantry 12. Detector array 26 is formed by detector elements 28, which are shown in more detail in FIG. 3 and discussed below. Detector elements 28 are radiation detectors that each produce a signal having a magnitude that represents and is dependent on the intensity of the attenuated x-ray beam after it has passed through object 18 being imaged. During a helical scan that acquires x-ray projection data, gantry 12 along with the x-ray source 22 and detector array 26 rotate within a plane and around object 18 about a center of rotation, while object 18 is moved through gantry 12 in a z-direction 32 perpendicular to the plane of rotation. In the exemplary embodiment, detector array 26 includes a plurality of detector rings each having a plurality of detector elements 28, the detector rings having an angular configuration corresponding to x-ray source 22.

Gantry 12 and x-ray source 22 are controlled by control system 14, which includes a gantry controller 36, an x-ray controller 38, a data acquisition system (DAS) 40, an image reconstructor 42, a conveyor controller 44, a computer 46, a mass storage-system 48, an operator console 50, and a display device 52. Gantry controller 36 controls the rotational speed and position of gantry 12, while x-ray controller 38 provides power and timing signals to x-ray source 22, and data acquisition system 40 acquires analog data from detector elements 28 and converts the data to digital form for subsequent processing. Image reconstructor 42 receives the digitized x-ray data from data acquisition system 40 and performs an image reconstruction process that involves filtering the projection data using a helical reconstruction algorithm.

Computer 46 is in communication with the gantry controller 36, x-ray controller 38, and conveyor controller 44 whereby control signals are sent from computer 46 to controllers 36, 38, 44 and information is received from controllers 36, 38, 44 by computer 46. Computer 46 also provides commands and operational parameters to data acquisition system 40 and receives reconstructed image data from image reconstructor 42. The reconstructed image data is stored by computer 46 in mass storage system 48 for subsequent retrieval. An operator interfaces with computer 46 through operator console 50, which may include, for example, a keyboard and a graphical pointing device, and receives output, such as, for example, a reconstructed image, control settings and other information, on display device 52.

Communication between the various system elements of FIG. 2 is depicted by arrowhead lines, which illustrate a means for either signal communication or mechanical operation, depending on the system element involved. Communication amongst and between the various system elements may be obtained through a hardwired or a wireless arrangement. Computer 46 may be a standalone computer or a network computer and may include instructions in a variety of computer languages for use on a variety of computer platforms and under a variety of operating systems. Other examples of computer 46 include a system having a microprocessor, microcontroller or other equivalent processing device capable of executing commands of computer readable data or program for executing a control algorithm. In order to perform the prescribed functions and desired processing, as well as the computations therefore (e.g., the execution of fourier analysis algorithm(s), the control processes prescribed herein, and the like), computer 46 may include, but not be limited to, a processor(s), memory, storage, register(s), timing, interrupt(s), communication interfaces, and input/output signal interfaces, as well as combinations including at least one of the foregoing. For example, computer 46 may include input signal filtering to enable accurate sampling and conversion or acquisitions of such signals from communications interfaces. As described above, exemplary embodiments can be implemented through computer-implemented processes and apparatuses for practicing those processes.

Figure 3:
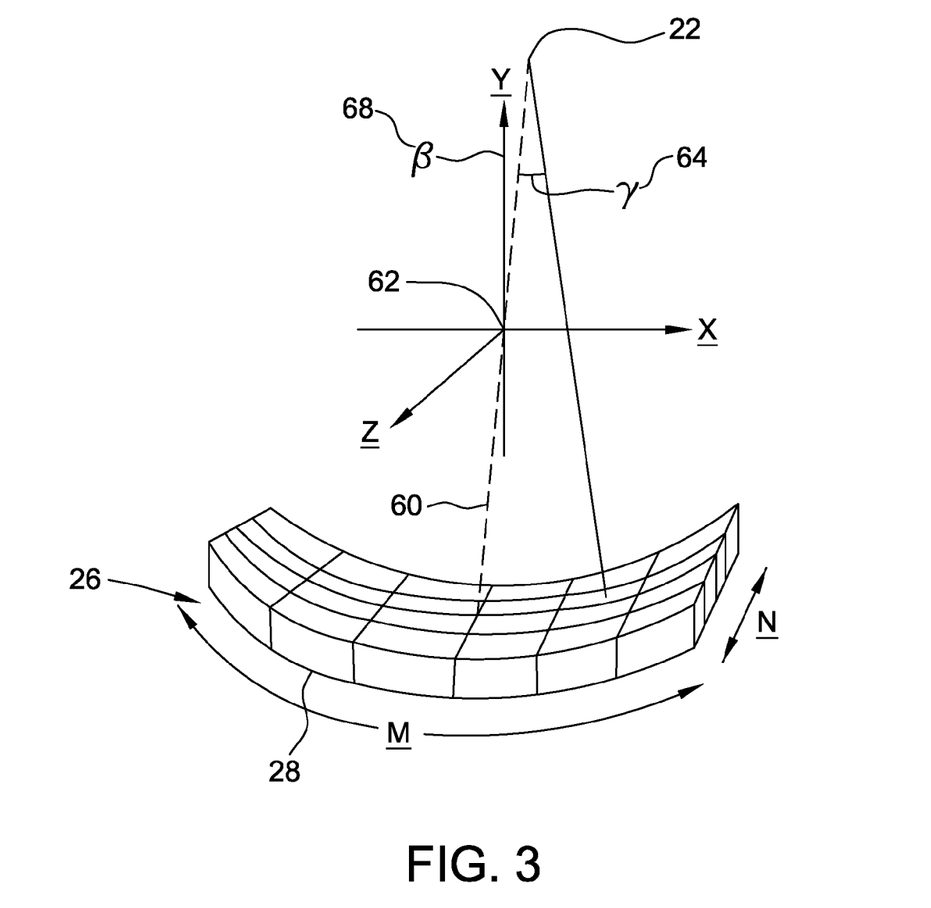
FIG. 3 is a schematic diagram of a detector array that may be used with the CT imaging system shown in FIG. 1.

Referring now to FIG. 3, an illustration of an x-ray beam having a beam axis (iso-ray) 60 that originates at x-ray source 22 and passes through center of rotation (iso-center) 62, relative to detector array 26, having detector elements 28 arranged in rows N and columns M, is provided. While FIG. 3 depicts only four rows (N=4 for four rings) and six columns (M=6 for six detectors per ring), it will be appreciated that any number of rows and columns may be employed as a matter of design choice. For example, some embodiments includes from sixteen to thirty-two rows of detector elements 28. Detector rows and detector rings are used interchangeably herein. As depicted in FIG. 3, a detector angle γ 64 is shown as an angle formed between an x-ray intersecting a given detector element 28 and iso-ray 60 which connects x-ray source 22 and the iso-center 62, and a projection angle β 68 is shown as an angle formed by iso-ray 60 with the y-axis.

Figure 4A:
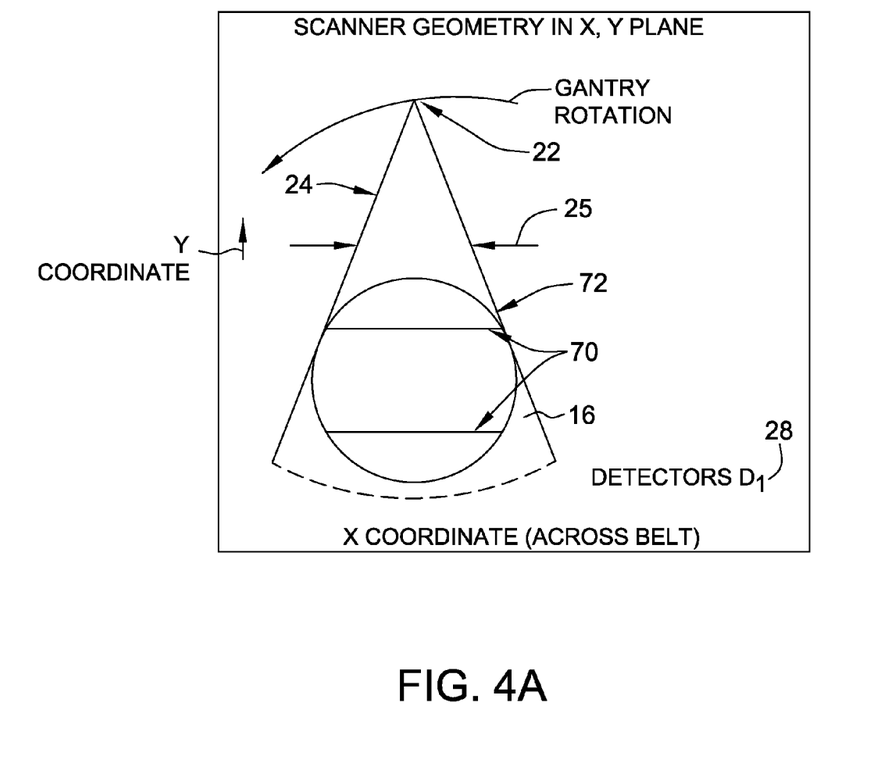
FIGS. 4A and 4B are schematic diagrams of the geometry of the CT imaging system shown in FIG. 1.
Figure 4B:
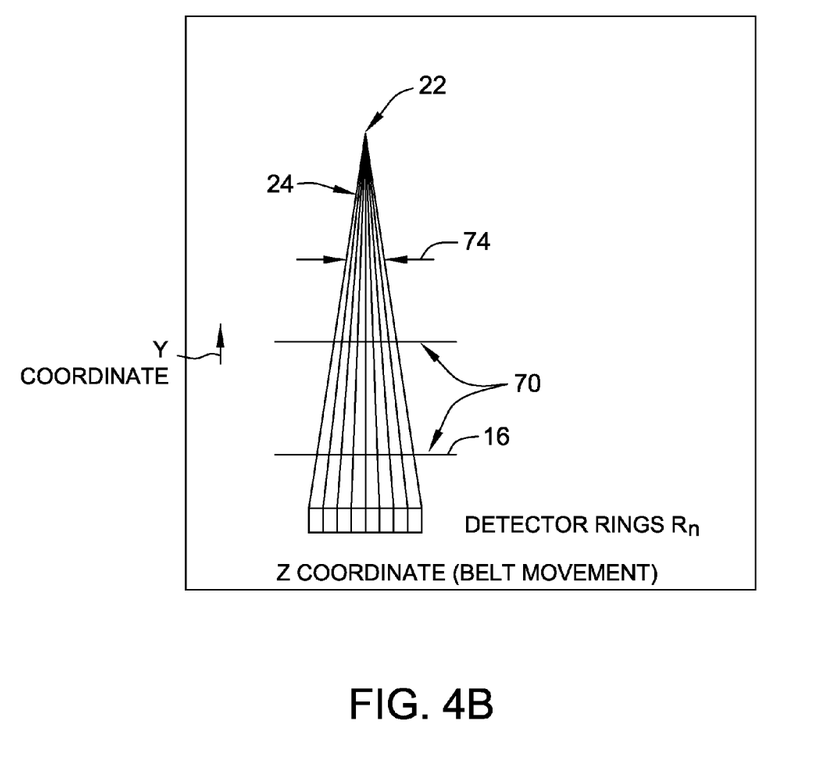

Referring now to FIGS. 4A and 4B, and in accordance with the exemplary embodiment, the data acquired at a single x-ray source position (also referred to herein as a view or tube position) is a set of fan beams 24 corresponding to a fan angle 25, with each x-ray beam at a slight angle to its neighbor. Also illustrated in FIGS. 4A and 4B is the bag or object volume 70, conveyor belt 16, a reconstruction circle 72, and a cone angle 74.

The systems and methods described herein facilitate generating a high-resolution projection image from un-reconstructed scan data using a helical cone beam CT scanner, such as CT imaging system 10. For each view, or source position, of x-ray source 22, the reconstruction algorithms described herein project raw data associated with a selected number rays onto an imaging surface, as described herein. Projecting a set of overlapping views creates a two-dimensional laminographic, or composite, image that resolves smaller features than can be resolved using data from any single view. The helical motion of the x-ray source 22 facilitates increased resolution in both dimensions in the laminographic image. Two exemplary embodiments for generating a laminographic image are described herein. Those of skill in the art will appreciate that modifications and/or variations on the specific embodiments described herein are within the spirit and scope of the disclosure.

Figure 5:
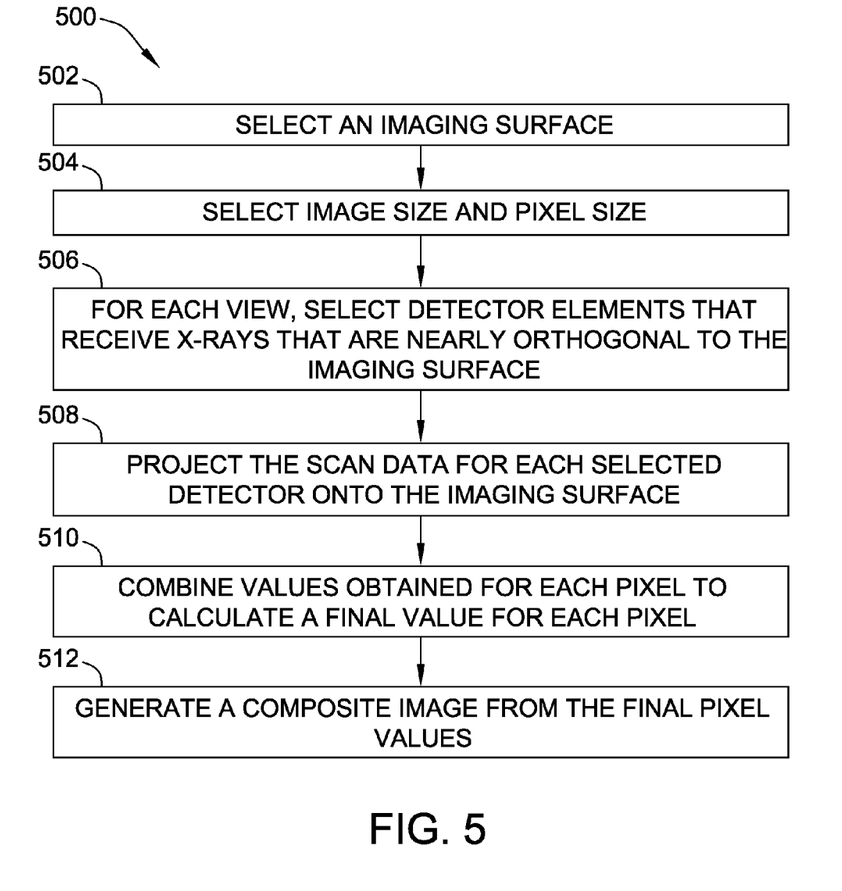
FIG. 5 is a flow chart of an exemplary method for generating a two-dimensional composite image of an object.
Figure 6:
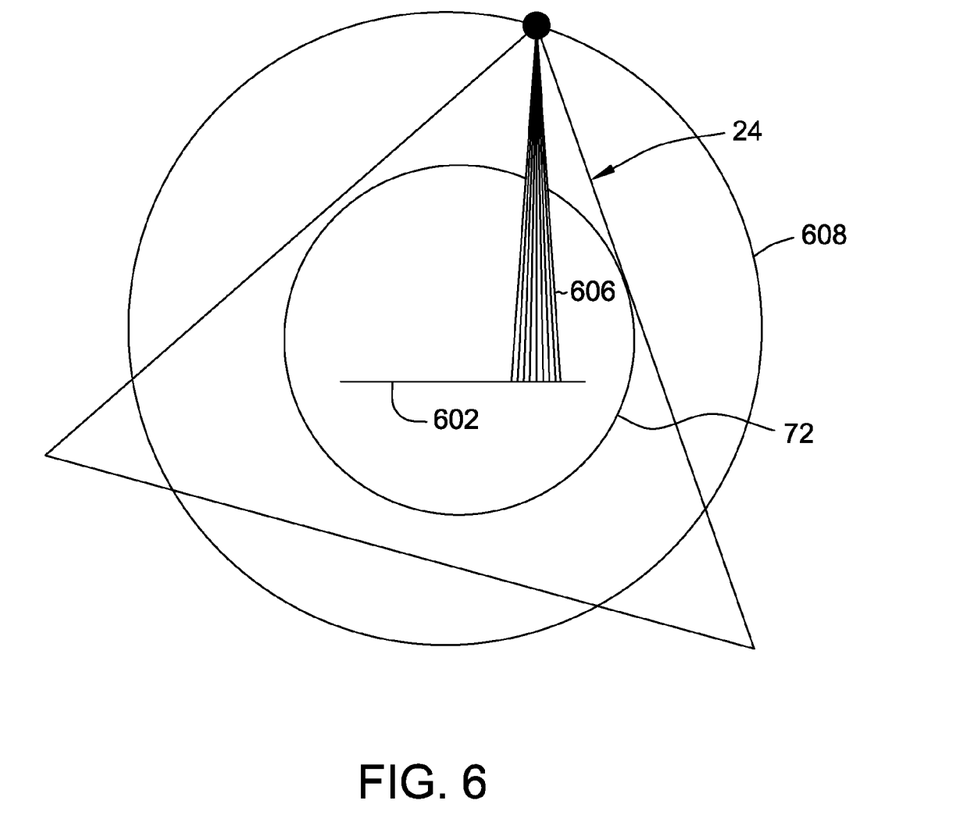
FIG. 6 is a schematic diagram illustrating operation of the method shown in FIG. 5.
Figure 7:
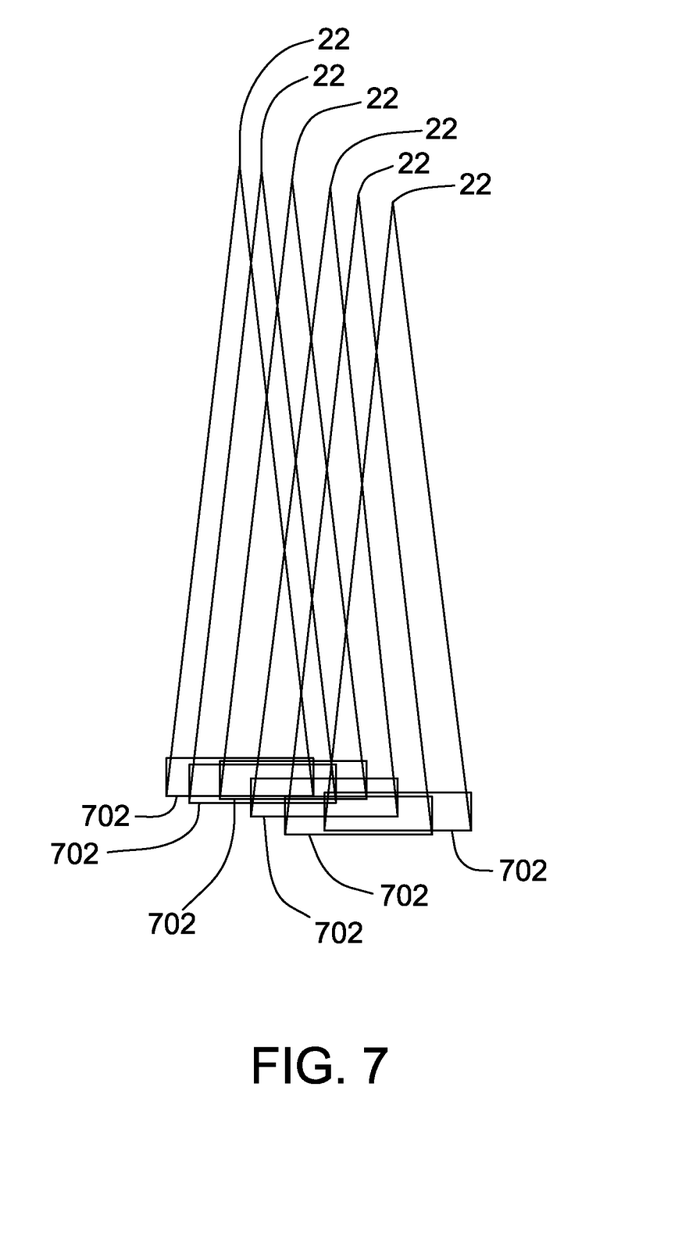
FIG. 7 is a schematic diagram illustrating operation of the method shown in FIG. 5.

FIG. 5 is a flow chart of an exemplary method 500 for generating a two-dimensional laminographic, or composite, image. FIGS. 6 and 7 are schematic diagrams illustrating operation of method 500. Method 500 may be performed, for example, using CT imaging system 10 (shown in FIG. 1). An imaging surface for the composite image is selected 502. The imaging surface may be a two-dimensional imaging plane, or may be a three-dimensional (i.e., non-planar) surface. Further, the imaging surface may be selected 502 by a user operating operator console 50, or may be selected 502 automatically by computer 46. For example, computer 46 may automatically select an imaging surface based on a height of the object that is determined from imaging data.

In FIG. 6, the imaging surface is an imaging plane 602 oriented parallel to and above belt 16 (shown in FIG. 1). For example, imaging plane 602 may be located approximately 5 centimeters (cm) above belt 16. Further, imaging plane 602 is located within CT reconstruction circle 72. Alternatively, the imaging surface may have any orientation and/or position that enables method 500 to function as described herein.

An image size and a pixel size are selected 504 for the laminographic image. In the exemplary embodiment, the spacing between adjacent pixels is smaller than the spacing between adjacent detector elements 28 in detector array 26. The image size and pixel size may be selected 504 by a user operating operator console 50, or may be selected 504 automatically by computer 46. In one example, the image is 1 meter wide by 1.5 meters long, with a pixel size of 1 square millimeter (mm) Alternatively, the image size and pixel size may have any dimensions that enable method 500 to function as described herein.

For each view that positions x-ray source 22 above or below the imaging surface, a set of detector elements 28 (shown in FIGS. 2-4) is selected 506. Specifically, detector elements 28 that receive x-rays that pass through the imaging surface at an orientation nearly orthogonal (or nearly parallel to another predetermined angle/viewing direction) to the imaging surface are selected 506. When the imaging surface is a non-planar surface, the direction "orthogonal" to the imaging surface may be, for example, a direction orthogonal to an average orientation of the imaging surface.

For example, as shown in FIG. 6, when the imaging surface is imaging plane 602, the selected 506 detector elements 28 are a subset of detector elements 28 that receive nearly vertical x-rays. For example, for imaging plane 602, the selected detector elements 28 may form a rectangle thirty two detectors elements 28 long in the Z direction and sixty detector elements 28 wide (corresponding to a beam 606 that is approximately three degrees wide in the cone angle direction and approximately six degrees wide in the fan angle direction).

The scan data for each selected 506 detector element 28 is projected 508 onto the imaging surface and more particularly, to a corresponding pixel on the imaging surface. To determine which detector elements 28 contribute to which pixels, interpolation and/or nearest neighbor techniques may be used. As noted above, these detector elements 28 are selected for each view in a path 608 of x-ray source 22 that positions x-ray source 22 above or below the imaging surface. For subsequent views, rectangles 702 formed by the selected 506 detector elements 28 overlap with one another, as shown in FIG. 7. Although FIG. 7 only shows views where x-ray source 22 is above belt 16, for a given pixel in the imaging surface, views above belt 16 and/or views below belt 16 may be used.

As such, scan data may be projected 508 onto a given pixel from multiple detector elements 28 over multiple views. Accordingly, in the exemplary embodiment, the one or more values acquired for each pixel by projecting 508 the scan data are combined 510 to obtain a final value. For example, the final value for a given pixel may be an average (e.g., weighted or unweighted) of all of the values obtained for that pixel throughout the different views. For a weighted average, for example, x-rays that are closer to orthogonal are given greater weight. Averaging the values acquired increases a signal to noise ratio by averaging out the noise. This facilitates increases the clarity of small objects.

Using the final values calculated for each pixel on the imaging surface, a computing device, such as computer 46, generates 512 the two-dimensional composite image. The composite image may be displayed to a user, for example, on display device 52 (shown in FIG. 2). Depending on a speed of belt 16, some pixels may have a single value or no values. For pixels that do not include any associated values, those pixels may be left blank in the final image, or interpolation techniques may be applied to generate values for those pixels.

Figure 8:
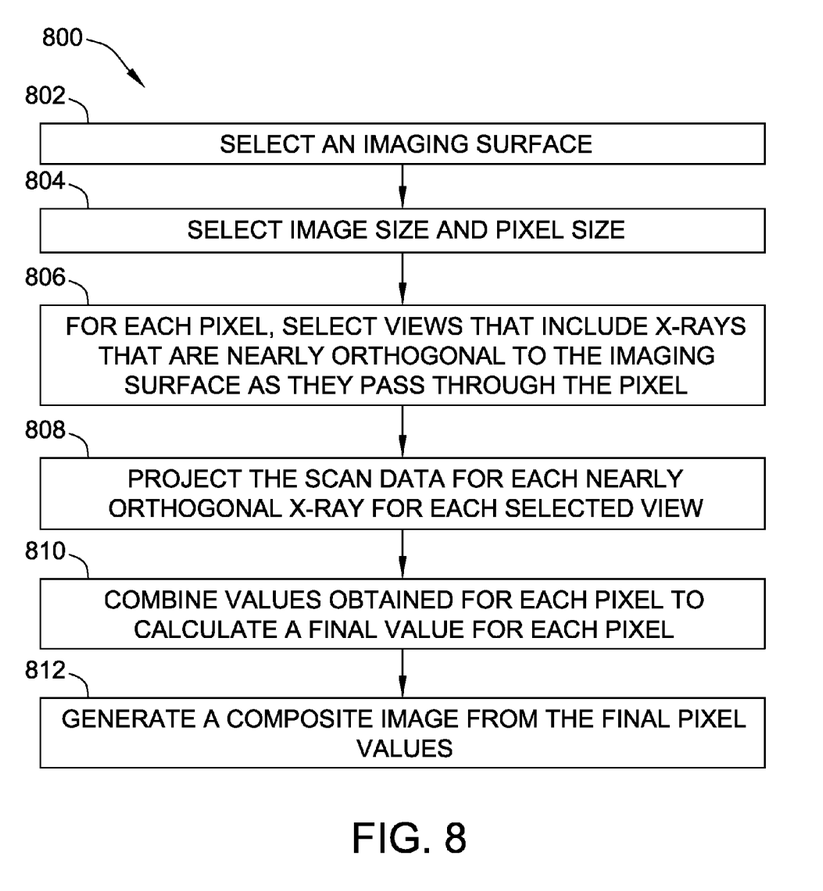
FIG. 8 is a flow chart of an alternative exemplary method for generating a two-dimensional composite image of an object.
Figure 9:
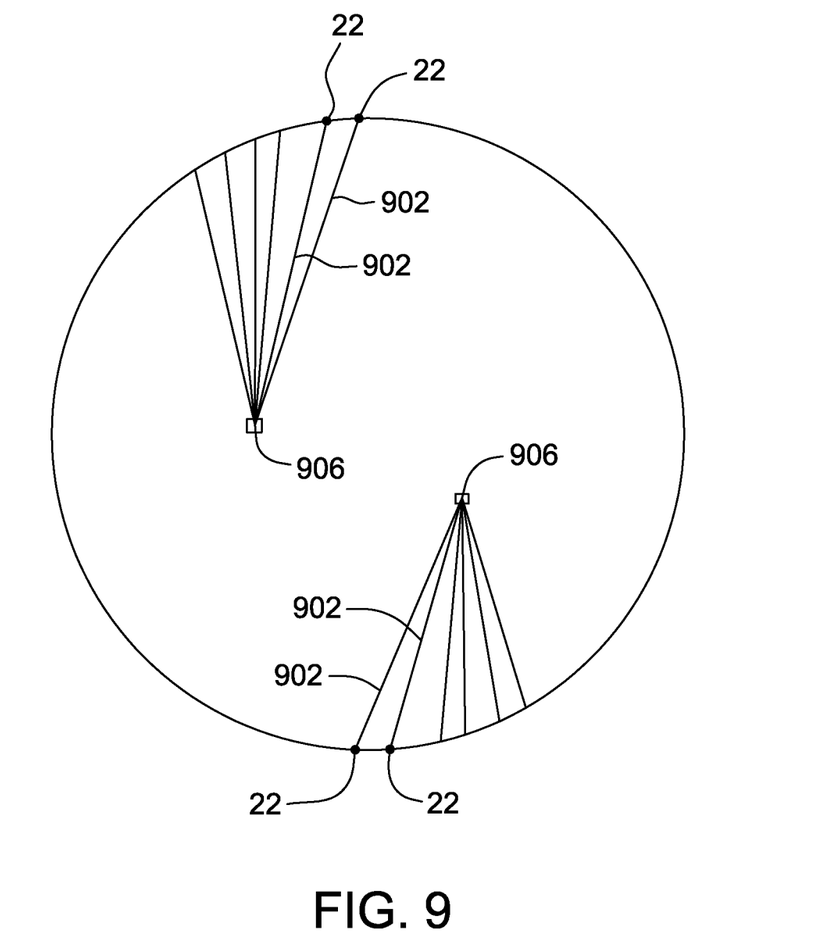
FIG. 9 is a schematic diagram illustrating operation of the method shown in FIG. 8.

FIG. 8 is a flow chart of an alternative exemplary method 800 for generating a composite image. FIG. 9 is a schematic diagram illustrating operation of method 800. Method 800 may be performed, for example, using CT imaging system 10 (shown in FIG. 1). The steps of selecting 802 an image surface and selecting 804 an image size and pixel size are substantially similar to selecting 502 an image surface and selecting 504 an image size and pixel size in method 500. Accordingly, selecting 802 an image surface and selecting 804 an image size and pixel size are not discussed in detail herein.

However, in contrast to the approach of method 500, in method 800, one or more views are selected 806 for each pixel on the imaging surface. Specifically, for each pixel, views at which x-ray source 22 emits an x-ray that is nearly orthogonal (or nearly parallel to another predetermined angle) to the imaging surface as the x-ray passes through the pixel are selected 806. In method 800, x-rays that are nearly orthogonal to the imaging surface may be, for example, x-rays oriented in a range from approximately 87° to 93° (i.e., +3° to −3° relative to the viewing direction) relative to the imaging surface, and may correspond to, for example, approximately twenty different views. FIG. 9 is a diagram illustrating a plurality of nearly orthogonal x-rays 902 from a plurality of different views 904 intersecting two different pixels 906.

The scan data for each nearly orthogonal x-ray from each selected 806 view is projected 808 onto the corresponding pixel on the imaging surface. Similar to method 500, to determine which detector elements 28 contribute to which pixels, interpolation and/or nearest neighbor techniques may be used. For multiple selected 806 views, multiple pieces of scan data will be projected 808 onto a given pixel. Accordingly, in the exemplary embodiment, the one or more values acquired for each pixel by projecting 808 the scan data are combined 810 to obtain a final value. For example, the final value for a given pixel may be an average (e.g., weighted or unweighted) of all of the values obtained for that pixel throughout the selected 506 views. For a weighted average, for example, x-rays that are closer to orthogonal are given greater weight. Averaging the values acquired increases the signal to noise ratio by averaging out the noise. This facilitates increasing the clarity of small objects.

Similar to method 500, using the final values calculated for each pixel on the imaging surface, a computing device, such as computer 46, generates 812 the composite image. The composite image may be displayed to a user, for example, on display device 52 (shown in FIG. 2). Depending on a speed of belt 16, some pixels may have a single value or no values. For pixels that do not include any associated values, those pixels may be left blank in the final image, or interpolation techniques may be applied to generate values for those pixels.

Whether selecting, for each of a plurality of views, detector elements that receive x-rays that are nearly orthogonal (or nearly parallel to some other non-parallel angle) to the imaging surface (as in method 500) or selecting views that include x-rays that are nearly orthogonal (or nearly parallel to some other non-parallel angle) to the imaging surface (as in method 800), the systems and methods described herein may both be described as selecting a viewing direction that is non-parallel to the imaging surface, and generating an image from x-rays that are within a pre-determined angle from parallel to the viewing direction.

In the exemplary methods, the viewing direction is orthogonal to the imaging surface. Alternatively, as noted above, the viewing direction may be oriented at other non-parallel angles relative to the imaging surface.

Using method 500 or method 800, a laminographic, or composite, image of an object may be generated. In some embodiments, multiple composite images of an object may be generated by using multiple imaging surfaces. For example, in one embodiment, a set of composite images is generated using a plurality of imaging planes oriented parallel to and above belt 16, each imaging plane set a different height above belt 16. Accordingly, the set of composite images generated is a set of horizontal slices of the object at varying heights. The set of images may be displayed on display device 52, and using operator console 50, a user may select an image in the set that appears to be the sharpest and/or that contains an item of interest (e.g., contraband). Alternatively, for "auto-focus" functionality, computer 46 may perform suitable image analysis techniques on the set of images to determine the sharpest image, and select and/or display the sharpest image.

Using the systems and methods described herein, a two-dimensional image of an object is generated. More specifically, an imaging surface for the object is selected, and a viewing direction that is non-parallel to the imaging surface is selected. Data values for x-rays that pass through pixels in the imaging surface and that are within a predetermined angle from parallel to the viewing direction is acquired. For each pixel, the data values are combined to calculate a final value. A two-dimensional image is generated from the final value. Combining data from multiple views facilitates improving a resolution of the generated image.

The systems and methods described herein may be used to detect contraband. As used herein, the term "contraband" refers to illegal substances, explosives, narcotics, weapons, special nuclear materials, dirty bombs, nuclear threat materials, a threat object, and/or any other material that a person is not allowed to possess in a restricted area, such as an airport. Contraband may be hidden within a subject (e.g., in a body cavity of a subject) and/or on a subject (e.g., under the clothing of a subject). Contraband may also include objects that can be carried in exempt or licensed quantities intended to be used outside of safe operational practices, such as the construction of dispersive radiation devices.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Exemplary embodiments of methods and systems for imaging an object are described above in detail. The methods and systems are not limited to the specific embodiments described herein, but rather, components of systems and/or steps of the methods may be used independently and separately from other components and/or steps described herein. Accordingly, the exemplary embodiment can be implemented and used in connection with many other applications not specifically described herein.

Technical effects of the systems and methods described herein include at least one of a) acquiring, for each pixel of a plurality of pixels in an imaging surface, data values for x-rays that pass through the pixel and are within a pre-determined angle from parallel to a viewing direction; (b) combining the data values acquired for each pixel to calculate a final value for each pixel; and (c) generating a two-dimensional image of an object based on the calculated final values for each pixel.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for generating a two-dimensional image of an object using a CT scanner, said method comprising:
   selecting an imaging surface for the object, the imaging surface including a plurality of pixels;
   selecting a viewing direction that is non-parallel to the imaging surface;
   rotating an x-ray source of the CT scanner around the object through a plurality of views, wherein the x-ray source projects x-rays towards a detector array opposite the x-ray source;
   for each pixel of the plurality of pixels:
     acquiring using the detector array, from the plurality of views, data values for x-rays that pass through the pixel and are within a pre-determined angle from parallel to the viewing direction; and
     combining, using a processing device, the data values acquired for the pixel while excluding other data values that do not correspond to the x-rays that pass through the pixel and are within the pre-determined angle to calculate a final value for the pixel; and
   generating the two-dimensional image of the object based on the calculated final values for each pixel.

2. A method in accordance with claim 1, wherein selecting an imaging surface comprises selecting an imaging plane.

3. A method in accordance with claim 1, wherein selecting an imaging surface comprises selecting a non-planar surface.

4. A method in accordance with claim 1, wherein rotating an x-ray source around the object comprises rotating the x-ray source around the object along a helical path.

5. A method in accordance with claim 1, wherein combining the data values acquired for the pixel comprises averaging the data values acquired for the pixel.

6. A method in accordance with claim 1, wherein acquiring data values comprises:
   selecting, for each view of the plurality of views, detector elements in the detector array that receive x-rays that are within the pre-determined angle from parallel to the viewing direction; and
   projecting scan data for each selected detector element onto the imaging surface.

7. A method in accordance with claim 1, rein acquiring data values comprises:
   selecting views of the plurality of views that include x-rays that are within the pre-determined angle from parallel to the viewing direction; and
   projecting the scan data from the selected views for each x-ray that is within the pre-determined angle from parallel to the viewing direction onto the imaging surface.

8. A method in accordance with claim 1, wherein selecting a viewing direction comprises selecting a viewing direction that is substantially orthogonal to the imaging surface.

9. A processing device for generating a two-dimensional image of an imaging surface of an object, the imaging surface including a plurality of pixels, said processing device configured to cause a computer to implement a method comprising:
   acquiring from a detector array communicatively coupled to said processing device, for each pixel of the plurality of pixels, data values for x-rays that pass through the pixel and are within a pre-determined angle from parallel to a viewing direction, wherein the viewing direction is non-parallel to the imaging surface, wherein the x-rays are emitted from an x-ray source that rotates around the object through a plurality of views, and wherein the data values for the pixel are acquired across the plurality of views;
   combining, using said processing device, the data values acquired for each pixel while excluding other data values that do not correspond to the x-rays that pass through the pixel and are within the pre-determined angle to calculate a final value for each pixel; and
   generating the two-dimensional image of the imaging surface based on the calculated final values for each pixel.

10. A processing device in accordance with claim 9, wherein the imaging surface is an imaging plane.

11. A processing device in accordance with claim 9, wherein the imaging surface is a non-planar surface.

12. A processing device in accordance with claim 9, wherein the x-ray source rotates around the object along a helical path.

13. A processing device in accordance with claim 9, wherein combining the data values acquired for each pixel comprises averaging the data values acquired for each pixel.

14. A processing device in accordance with claim 9, wherein acquiring data values comprises:
   selecting, for each view of the plurality of views, detector elements in the detector array that receive x-rays that are within the pre-determined angle from parallel to the viewing direction; and
   projecting scan data for each selected detector element onto the imaging surface.

15. A processing device in accordance with claim 9, wherein acquiring data values comprises:
   selecting views of the plurality of views that include x-rays that are within the pre-determined angle from parallel to the viewing direction; and projecting the scan data from the selected views for each x-ray that is within the pre-determined angle from parallel to the viewing direction onto the imaging surface.

16. A processing device in accordance with claim 9, wherein the viewing direction is substantially orthogonal to the imaging surface.

17. A CT system for imaging an object, said CT system comprising:
- a CT scanner comprising:
  - an x-ray source configured to rotate around the object through a plurality of views and project x-rays towards the object; and
  - a detector array positioned opposite said x-ray source; and
- a storage medium communicatively coupled to said detector array and encoded with machine readable computer program code for generating a two-dimensional image of an imaging surface of the object, the imaging surface including a plurality of pixels, the storage medium including instructions for causing a computer to implement a method comprising:
  - acquiring from said detector array, for each pixel of the plurality of pixels, data values for x-rays that pass through the pixel and are within a pre-determined angle from parallel to a viewing direction, wherein the viewing direction is non-parallel to the imaging surface, and wherein the data values for the pixel are acquired across the plurality of views;
  - combining, using the computer, the data values acquired for each pixel while excluding other data values that do not correspond to the x-rays that pass through the pixel and are within the pre-determined angle to calculate a final value for each pixel; and
  - generating the two-dimensional image of the imaging surface based on the calculated final values for each pixel.

18. A CT system in accordance with claim 17, wherein the imaging surface is an imaging plane.

19. A CT system in accordance with claim 17, wherein the imaging surface is a non-planar surface.

20. A CT system in accordance with claim 17, wherein combining the data values acquired for each pixel comprises averaging the data values acquired for each pixel.

* * * * *